(12) United States Patent
Cronenberg et al.

(10) Patent No.: US 6,749,812 B2
(45) Date of Patent: Jun. 15, 2004

(54) AUTOMATIC PIPETTE DETIPPING

(75) Inventors: Richard A. Cronenberg, Mahwah, NJ (US); Dennis Mitchell, Huntington, NY (US)

(73) Assignee: Vistalab Technologies, Mt. Kisco, NY (US)

( * ) Notice: Subject to any disclaimer, the term of this patent is extended or adjusted under 35 U.S.C. 154(b) by 220 days.

(21) Appl. No.: 09/873,842

(22) Filed: Jun. 4, 2001

(65) Prior Publication Data

US 2002/0001545 A1 Jan. 3, 2002

Related U.S. Application Data

(60) Provisional application No. 60/214,206, filed on Jun. 26, 2000.

(51) Int. Cl.[7] .............................. B01L 3/02; G01N 1/10
(52) U.S. Cl. ...................... 422/100; 422/100; 436/180; 873/864; 873/863.32; 873/864.01; 873/864.11; 873/864.14
(58) Field of Search ................ 422/100, 99; 73/863.32, 73/863.25, 864, 864.01, 864.11, 864.14

(56) References Cited

U.S. PATENT DOCUMENTS

| | | | |
|---|---|---|---|
| 3,732,735 A | 5/1973 | Cohen | |
| 3,853,012 A | 12/1974 | Scordato et al. | |
| 3,933,048 A | 1/1976 | Scordato | |
| 3,954,014 A | 5/1976 | Andrews, Jr. et al. | |
| 3,991,617 A | 11/1976 | d'Autry | |
| 4,151,750 A | 5/1979 | Suovaniemi et al. | |
| 4,164,870 A | 8/1979 | Scordato et al. | |
| 4,257,267 A | 3/1981 | Parsons | |
| 4,283,950 A * | 8/1981 | Tervamaki | 73/864.14 |
| 4,478,094 A | 10/1984 | Salomaa et al. | |
| RE32,210 E | 7/1986 | d'Autry | |
| 4,821,586 A | 4/1989 | Scordato et al. | |
| 4,967,604 A | 11/1990 | Arpagaus et al. | |
| 5,104,625 A | 4/1992 | Kenney | |
| 5,403,553 A | 4/1995 | Heinonen | |
| 5,614,153 A * | 3/1997 | Homberg | 422/100 |
| 5,620,661 A | 4/1997 | Schurbrock | |
| 5,807,524 A | 9/1998 | Kelly et al. | |
| 5,970,806 A | 10/1999 | Telimaa et al. | |
| 6,197,259 B1 | 3/2001 | Kelly et al. | |
| 6,299,841 B1 * | 10/2001 | Rainin et al. | 422/100 |
| 6,324,925 B1 | 12/2001 | Suovaniemi et al. | |
| 6,532,837 B1 | 3/2003 | Magussen, Jr. et al. | |
| 2003/0074989 A1 * | 4/2003 | Magnussen et al. | 73/864.14 |
| 2003/0082078 A1 * | 5/2003 | Rainin et al. | 422/100 |
| 2003/0099578 A1 * | 5/2003 | Cote et al. | 422/100 |

FOREIGN PATENT DOCUMENTS

| | | |
|---|---|---|
| EP | 0 421 785 A2 | 4/1991 |
| EP | 0 437 906 A1 | 7/1991 |
| GB | 2 172 218 A | 9/1986 |
| WO | WO 01/57490 A1 | 8/2001 |

OTHER PUBLICATIONS

"The Automatic Pipette", American Diagnostica.
Handi–Pet Pipetting Gun, General Diagnostics, 1973.
Eppendorf EDOS 5221, Instruction Manual, Eppendorf, Germany.

* cited by examiner

*Primary Examiner*—Jill Warden
*Assistant Examiner*—Brian Gordon
(74) *Attorney, Agent, or Firm*—Baker & McKenzie

(57) ABSTRACT

Mechanisms are provided for automatically removing tips from a pipette nozzle and/or for detecting the type of tip mounted to the nozzle. For detipping, mechanical energy is stored when the tip is mounted to the nozzle and is released when the tip is to be removed to facilitate removal thereof. A mechanism is preferably provided which limits the force with which the tip is mounted to the nozzle and an overforce mechanism may be provided to facilitate removal of a stuck tip. For detecting tip type, each tip type has a different base configuration which results in a different relative displacement between the nozzle and a surrounding component as a result of the tip contacting both during tip mounting, the difference in relative displacement being detected to identify tip type.

27 Claims, 10 Drawing Sheets

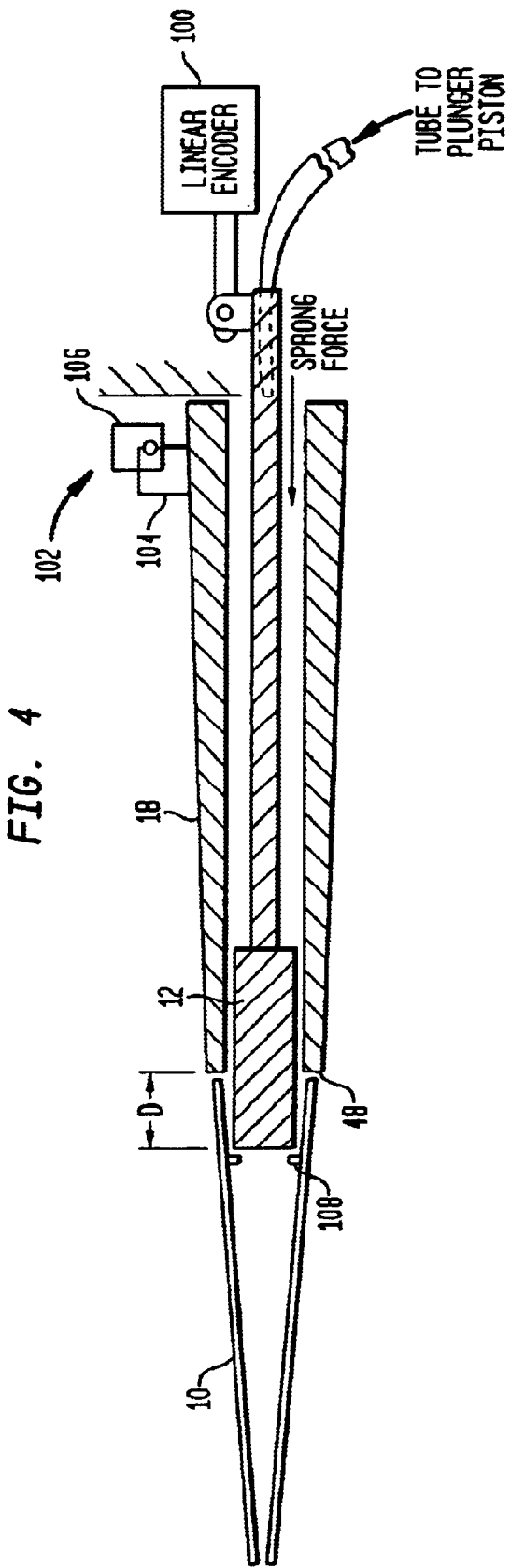

AUTOMATIC PIPETTE DETIPPING

RELATED APPLICATIONS

This application claims priority from provisional application serial No. 60/214,206 filed Jun. 26, 2000.

FIELD OF THE INVENTION

This invention relates to pipettes, and more particularly to pipettes having automatic mechanisms for identifying and/or removing tips.

BACKGROUND OF THE INVENTION

Pipettes are commonly utilized to aspirate a fluid from one container or other source and to dispense the fluid to a second container or other receptacle. Since the fluid being aspirated and dispensed is frequently analyzed or otherwise tested after being dispensed, and in order for such testing or analysis to be accurate, it is important that a sample not be contaminated by fluid from a prior aspirated sample. While it is possible to wash a pipette tip between aspirations in order to reduce or eliminate such contamination, and for some pipette systems, particularly those utilizing fluid displacement, this is frequently done, washing the tips is expensive and time-consuming, and it is frequently difficult to remove all contaminants. Therefore, for many pipettes, particularly air displacement pipettes, it is cheaper and easier to replace the pipette tip after each use.

However, when a pipette tip is mounted to the nozzle, it is important that the tip be mounted with sufficient force to seal the nozzle so that fluid being aspirated and dispensed does not leak around the tip-nozzle junction, thereby preventing accurate quantities of fluid from being aspirated and dispensed, and the tip must be mounted with sufficient force to prevent the tip from falling off. However, if the tip is mounted with too much force, it can become difficult to remove the tip from the nozzle after use, resulting in significant strain on the operator's hand. For this and other reasons, an operator working in a laboratory or other facility where large numbers of tips are replaced each day may experience repetitive stress injuries with current pipette designs as a result of repeated tip removals.

Heretofore, control on the force applied in mounting a tip to a nozzle has generally relied on the skill of the person doing the mounting. Thus, while for an illustrative embodiment, only two pounds of force may be required to properly mount a tip to the nozzle, operators may inadvertently be applying 10 to 15 pounds of force in mounting the nozzle, making nozzle removal far more difficult than necessary. However, without tactile guidance, an operator might overcompensate for this problem and not properly mount a nozzle. Further, while some tip removal mechanisms have existed for pipettes in the past, these have generally been manually operated and, since they have generally not controlled tip mounting force, they have frequently required that substantial force be applied by, for example, the operator's thumb to successfully effect tip removal. This operation is therefore another potential cause of repetitive stress injuries. Alternatively, such tip removal schemes have been motor driven, increasing the size, cost and complexity of the pipette.

A related problem is that there are a variety of tips available for use with a given pipette and the pipette volume settings, particularly where these settings are automatically performed, need to be slightly adjusted for some tips to obtain the desired volumes of aspirated and/or dispensed fluid. The tips may for example have different length, volume, orifice diameter/size, shape and/or surface treatment (for example a low liquid retention coating). The tips may also be filtered or unfiltered, and if filtered, may have various special filtering elements, the presence and nature of filtering elements being a major factor in requiring volume adjustments for the pipette. While provision may be made for the user to input information on the tip being used either on the pipette or on a processor used therewith, this can be burdensome for the operator where a large number of pipetting operations are being performed. It also provides a source of pipetting error where the operator either forgets to identify a special tip used for a given operation or makes an erroneous entry, either because the operator doesn't know the tip used or enters tip information incorrectly. It is also possible that the operator may select the wrong tip for a particular pipetting operation. It would therefore be preferable if the pipette could easily and quickly identify the tip being mounted as part of the tip mounting process without requiring any operator input, and could provide some type of feedback to the operator, for example when there is a change in tip used, to minimize inadvertent use of the wrong tip.

A need therefore exists for improved pipettes which overcome the various tip mounting, tip removal and tip identification problems identified above.

SUMMARY OF THE INVENTION

The tip mounting and removal problems indicated above are generally overcome in accordance with the teachings of this invention by storing part of the force used by the operator to mount the tip to a nozzle, actively limiting the force with which the tip is mounted to the nozzle, providing a sensory feedback to the operator when the tip is properly positioned on the nozzle and releasing the mechanical energy stored during the mounting of the tip in response to operator activation to facilitate the automatic removal of the tip. An overforce capability may be provided to supplement the stored energy for the removal of a stuck tip. Mechanisms used for the above may also be utilized in solving the tip identification problem.

More specifically, the invention provides a mechanism for facilitating the removal of a tip from a pipette nozzle which includes a spring loaded ejector sleeve through which the nozzle passes, the sleeve terminating near the end of the nozzle to which the tip is mounted when the sleeve is in a normal position, the sleeve being moved away from the end of the nozzle against the spring load when the tip is mounted to the nozzle. The sleeve includes a first latch portion which mates with a second latch portion of the pipette when the sleeve is in a retracted position to which it is moved when a tip is properly mounted to the nozzle to hold the sleeve in the retracted position against the spring load, a third latch portion being provided which is operable to unmate the first and second latch portions, freeing the sleeve to return in response to the spring load to its normal position. The sleeve engages the tip before reaching the normal position to facilitate removal of the tip. The tip removal mechanism may include an overforce mechanism operable to supplement the spring load in moving the sleeve to its normal position against a stuck tip to further facilitate removal of the tip. For one embodiment, the first latch portion is a keyhole slot formed in the sleeve, the second latch portion is a detent having a large portion which fits in an enlarged portion of the slot when the sleeve is in its retracted position and a small portion sized to fit in a narrow portion of the slot, the narrow portion being adjacent to the detent except when the sleeve is in the retracted position. For this embodiment, the third latch portion is a button operable for moving the small portion of the detent into the slot to unlatch the sleeve. For this embodiment, the detent may be spring-biased to move the large portion of the detent into the slot. For another embodiment, the first latch portion is a projection at a proximal end of the sleeve, the second latch portion is a mating lip on a latch plate biased to have the lip engage the projection when the sleeve is in its retracted position and the third latch portion is a portion of the latch plate which is manually operable to move the plate against its bias to move the lip away from the projection, permitting the sleeve to return to its normal position. For this embodiment, an angled surface on the plate may be provided which is positioned to engage an angled surface associated with the sleeve when the latch plate is moved beyond the point where the lip no longer engages the projection, the interaction of the two angled surfaces supplementing the spring load in moving the sleeve to its normal position against a stuck tip to further facilitate removal of the tip.

The tip removal mechanism preferably also includes a mechanism for controlling the force with which a tip is mounted to the nozzle. This mechanism for controlling may include mounting the nozzle to be movable away from a tip mounting force and against a bias spring. For this embodiment, the bias spring preferably has less load than the spring load applied to the ejector sleeve.

The ejector sleeve is preferably moved away from the tip receiving end of the nozzle by the tip. Alternatively, where tips are mounted in a rack having a protrusion adjacent each tip, the ejector sleeve may be moved away from the end of the nozzle by the protrusion adjacent the tip being mounted. For preferred embodiments, the mating of the first and second latch portions results in an operator perceptible feedback output, for example an audio, tactile or visual feedback output.

The invention also includes a mechanism for facilitating the removal of a pipette tip from a pipette nozzle which includes an ejector normally biased to a first position near an end of the nozzle to which the tip is mounted and movable as the tip is mounted to the nozzle against the bias, the ejector reaching a retracted position when the tip is fully mounted; and a latch for maintaining the ejector in the retracted position, the latch including a selectively operable latch release, the bias returning the ejector to its first position when the latch release is operated to facilitate ejection of the tip mounted to the nozzle. An overforce mechanism may be provided which is operable to supplement the bias in moving the ejector to its normal position against a stuck tip to further facilitate removal of the tip. A mechanism is preferably also provided for controlling the force with which the tip is mounted to the nozzle. There may also be a plurality of different tip types, each of which contacts both the ejector and the nozzle as it is mounted to the nozzle and moves against a bias force, each tip having a different base configuration which results in a difference in the relative displacement of the nozzle to the ejector. A mechanism can be provided for detecting such difference in relative displacement to identify tip type.

More generally, the invention includes a mechanism for facilitating the removal of a pipette tip from a pipette nozzle including a mechanism which stores mechanical energy when a tip is mounted to the nozzle and which releases the stored mechanical energy when the tip is to be removed to facilitate removal thereof. The mechanism for storing may include a latching mechanism operative when the mechanical energy is fully stored, with an operator detectable output being generated when the latching mechanism operates. A mechanism is preferably also provided which limits the force with which the tip is mounted to the nozzle and an overforce mechanism may also be provided for further facilitating removal of a stuck tip.

The invention may also include a mechanism for detecting the type of pipette tip being mounted to a pipette nozzle which includes a sleeve mechanism surrounding the nozzle, at least one of the sleeve mechanism and nozzle being mounted to be selectively retracted when in contact with a tip as a tip is pressed on the nozzle to be mounted thereto, each tip type having a different base configuration which results in a difference in the relative displacement of the nozzle to the sleeve mechanism, a mechanism being provided for detecting such difference in relative displacement to thus identify tip type. Where the sleeve has a selected stroke, the mechanism for detecting may include a sensor generating an output when the sleeve is retracted for its selected stroke and a detector for nozzle retraction, the detector output when the sensor generates an output being indicative of tip type.

The foregoing and other objects, features and advantages of the invention will be apparent from the following more detailed description of preferred embodiments of the invention as illustrated in the accompanying drawings, the same or similar reference numerals being used for comparable elements in the various figures.

DESCRIPTION OF THE DRAWINGS

FIG. 4 is a side cut-away view of an alternative tip-identification embodiment of the invention.

DESCRIPTION OF THE INVENTION

Figure 1A:
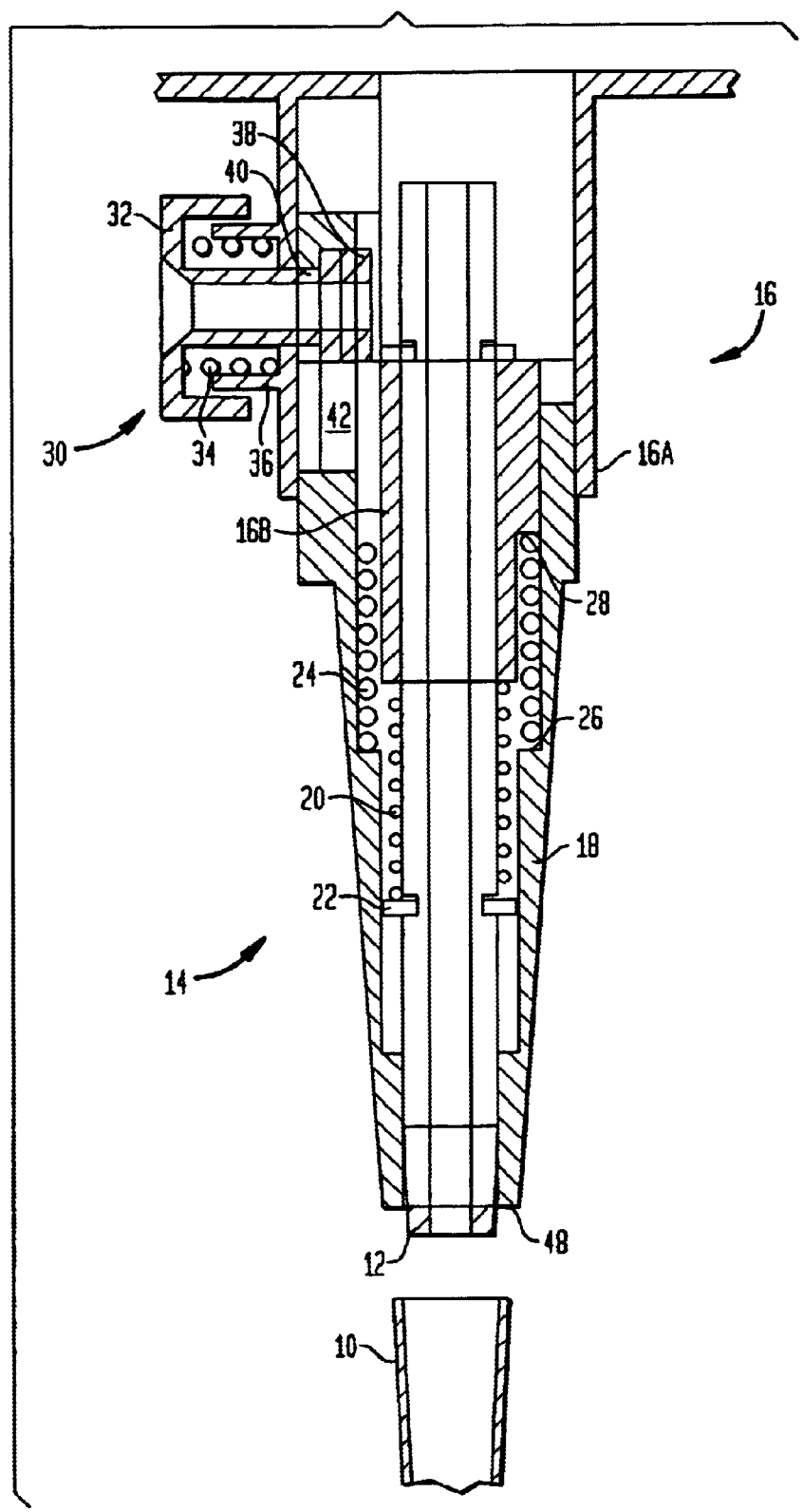
FIGS. 1A and 1B are side sectional views of a first embodiment of the invention shown in the released and latched positions respectively.
Figure 1B:
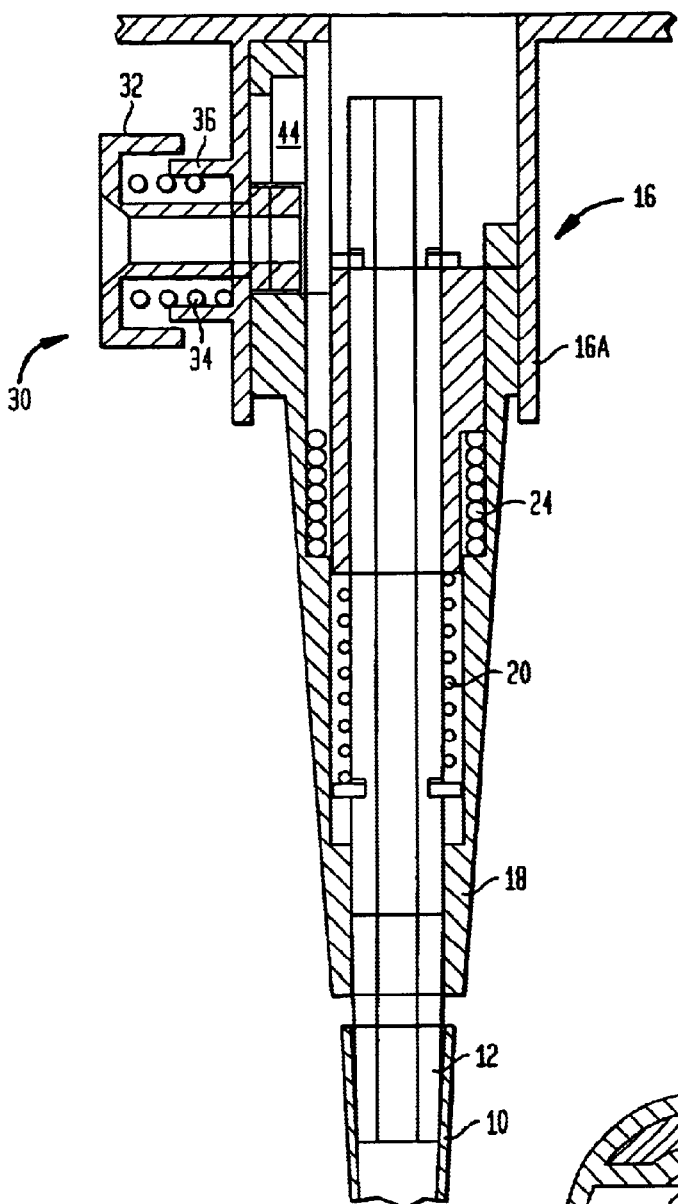
Figure 1C:
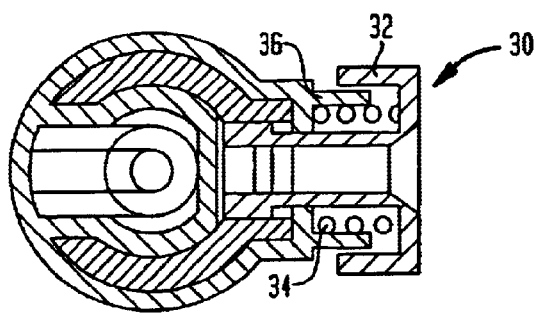

Referring to FIGS. 1A–1C, a first embodiment of the invention is shown wherein a tip 10 is mounted to a nozzle 12 which is part of a nozzle assembly 14. Assembly 14 includes a housing 16 having an outer sleeve 16A and an inner sleeve 16B. An ejector sleeve 18 surrounds nozzle 12, extending to a point near the distal end of the nozzle to which tip 10 is mounted, and fits at its proximal end between sleeves 16A and 16B of housing 16. Nozzle 12 is spring biased to the released position shown in FIG. 1A by a compression spring 20 extending between ring 22 fixed to nozzle 12 and the end of housing sleeve 16B. Ejector sleeve 18 is also spring biased to the released position of FIG. 1A by a compression spring 24 extending between an interior shoulder 26 of sleeve 18 and a shoulder 28 on inner housing sleeve 16B. In order for nozzle 12 to be movable as discussed herein, a flexible connection, for example a flexible hose, should be provided connecting the nozzle to its drive piston or other drive mechanism for aspiration and dispensing.

A latch mechanism 30 is provided which includes a button 32 mounted in outer sleeve 16A of the housing. Button 32 is biased toward the latched position shown in FIG. 1B by compression spring 34 mounted inside collar 36 extending from housing sleeve 16A, spring 34 extending between an outside wall of housing sleeve 16A and an inside wall of button 32. Button 32 has an enlarged, generally circular, inner end 38 and a narrower shaft portion 40 connecting the large end 38 to the remainder of the button 32. Sleeve 18 has a keyhole slot formed on the side thereof adjacent button 32, the slot having an enlarged forward portion 42 which is slightly larger than enlarged tip 38 of button 32, and a narrower rear portion 44 (FIG. 1B) which is slightly larger than shaft portion 40 of the latch button 32, but significantly smaller than enlarged portion 38.

In operation, the nozzle assembly 14 is initially in the released position shown in FIG. 1A. When the operator places a tip 10 over the end of nozzle 12 and starts to push down to mount the tip 10 on the nozzle 12, the first thing that happens is that the bottom of tip 10 engages the distal or outer end 48 of ejector sleeve 18, pushing sleeve 18 into housing 16 between housing sleeve 16A and 16B against the bias force of spring 24. As force continues to be exerted on tip 10 to mount it to nozzle 12, the tip 10 eventually makes contact with the nozzle 12 and becomes mounted thereto. Once the force exerted through tip 10 on nozzle 12 exceeds the bias force of spring 20, nozzle 12 moves rearward in housing 16 against the bias of spring 20, preventing excessive force from being applied to mount tip 10 to nozzle 12. The force with which the tip is mounted to the nozzle 12 is thus carefully controlled so as to be enough to seal the nozzle/tip joint and to keep the tip 10 in place, while still leaving the tip 10 easily removable. As tip 10 continues to be pushed against nozzle 12, sleeve 18 is ultimately moved against the bias of spring 24 to a position where the enlarged portion 42 of the slot in sleeve 18 is adjacent large portion 38 of button 32. When this happens, button 32 is moved outward under the bias force of spring 34 to move enlarged portion 38 into opening 42 in ejector sleeve 18, thereby latching nozzle assembly 14 in the latched position shown in FIG. 1B. The click from latch 30 engaging provides an audible feedback to the operator, and the movement of button 32 also provides a tactile and visual feedback to the operator, that the tip 10 is fully mounted so that the operator may terminate the mounting operation. If the user continued to exert force after latching occurs, sleeve 48 ultimately bottoms against housing 16, thus limiting travel of tip 10 and limiting the mounting force on the tip 10 to that exerted by compressed spring 20. When the operator releases tip 10, nozzle 12 is moved by its bias spring 20 to the position shown in FIG. 1B, this being the final position of the nozzle assembly 14 with the tip 10 mounted and the assembly in its latched position.

When the aspiration and/or dispensing operation has been completed and it is desired to eject tip 10 from nozzle 12, the operator presses on button 32 to move enlarged portion 38 of the button out of enlarged portion 42 of the keyhole slot in sleeve 18. This unlatches ejector sleeve 18, permitting spring 24 to return the ejector sleeve to the released position of FIG. 1A. It can be seen from the figures that before ejector sleeve 18 reaches its released position, upper shoulder 48 of the ejector sleeve engages the bottom surface of tip 10. By selecting springs 20 and 24 such that spring 24 has significantly greater force than spring 20, for example spring 24 being a three-pound spring and spring 20 a two-pound spring, the force with which the ejector sleeve strikes tip 10 when the ejector sleeve is unlatched will be sufficiently greater than the controlled force with which the tip is mounted to the nozzle to result in the tip being automatically ejected from nozzle 12 by ejector sleeve 18 as it moves to its released position. Thus, the energy stored in spring 24 when tip 10 is mounted to nozzle 12 is utilized to automatically eject the tip when use of the tip has been completed.

FIGS. 2A–2D show an alternative embodiment of the invention which has an alternative latch mechanism 30' and also has an overforce feature not present in the embodiment of FIGS. 1A–1B. In particular, sleeve 18', rather than having a keyhole slot formed in its side, has a flange 60 with a shoulder 62 and an angled outer wall 64 formed at the bottom or inner end thereof. Latch 30' includes a slotted plate 66 which is biased to the latched position shown in FIG. 2B by tension spring 67 extending between posts fixed to housing portion 16C and to plate 66. Plate 66 also has an extended groove 84 formed on the inner side thereof, which groove 84 may for example extend for approximately 90° and which has an upper shoulder 70. Plate 66 slides on a housing member 16C and is guided by four pins 72 extending from housing member 16C, which pins fit in mating slots 74 in plate 66 (see FIG. 2D). Plate 66 has an insert 76 with an angled inner wall 78. Plate 66 also has an opening 80 in its top through which sleeve 18' and nozzle 12 extend.

Figure 2A:
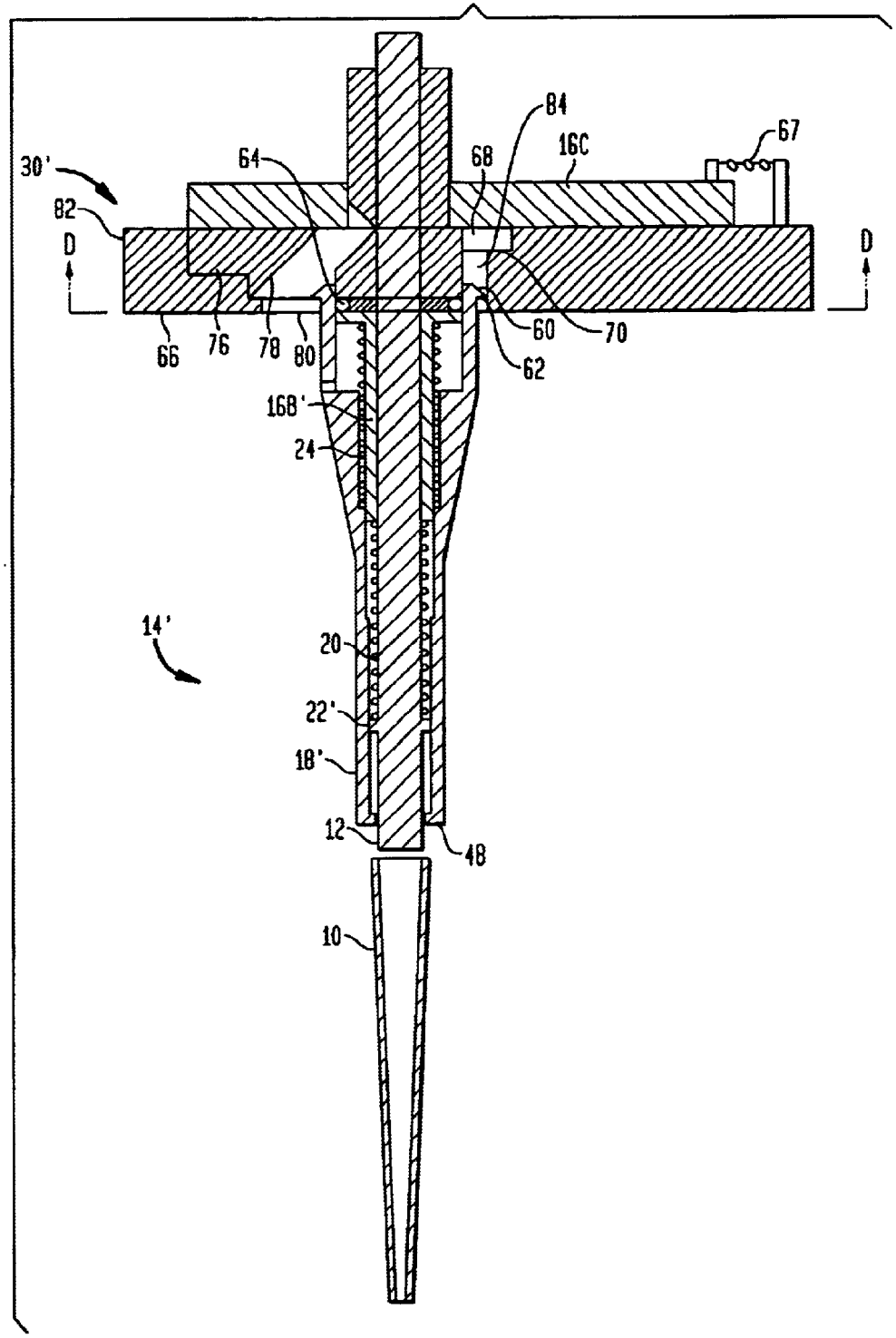
FIGS. 2A, 2B and 2C are side sectional views for an alternative embodiment of the invention shown in the released, latched and overforce positions respectively.
Figure 2B:
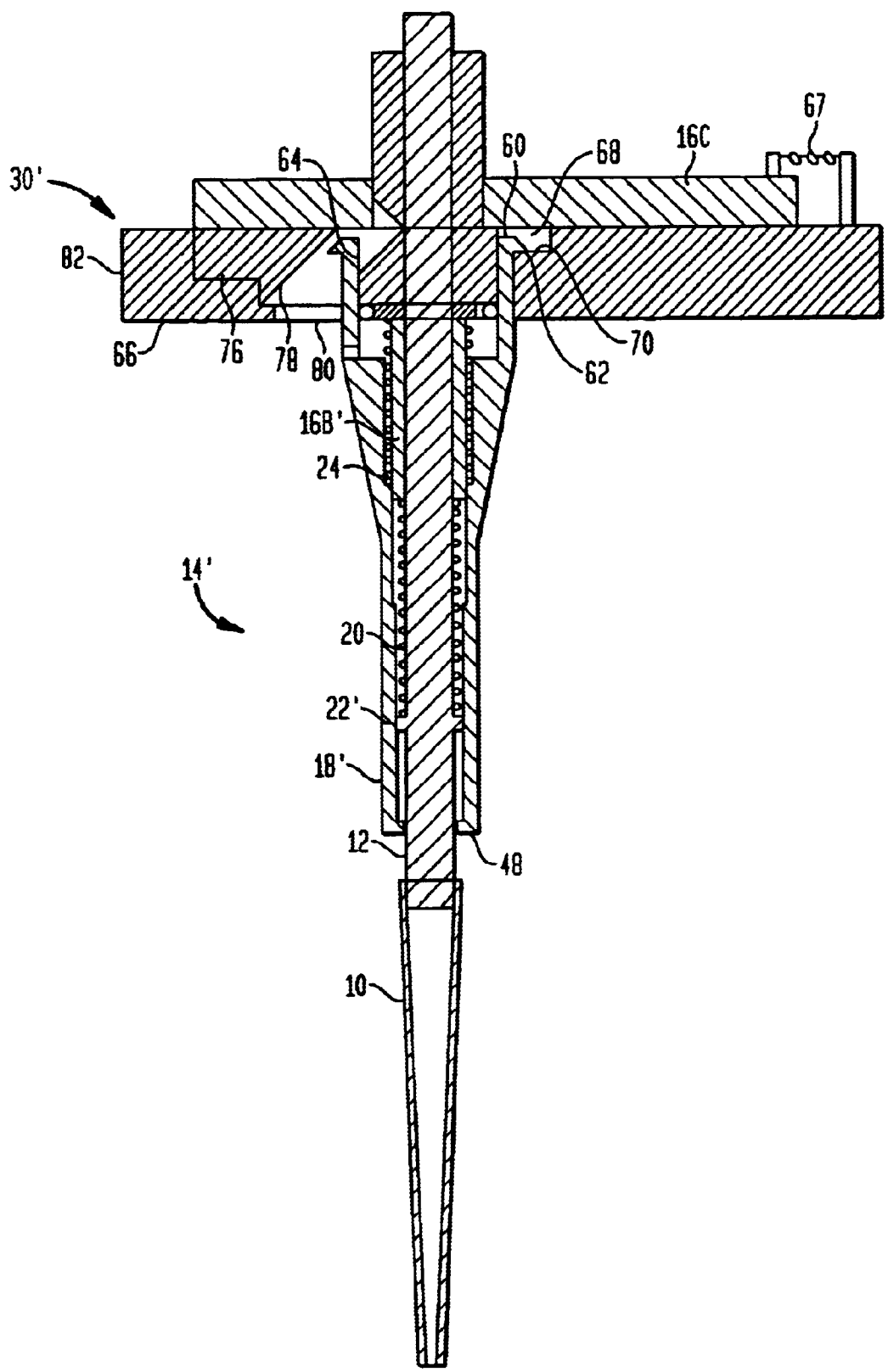

In operation, latch assembly 30' is initially in the released position shown in FIG. 2A. As for the embodiment of FIGS. 1A–1B, when tip 10 is mounted over nozzle 12, it initially makes contact with shoulder 48 of sleeve 18' moving the sleeve into the nozzle assembly 14' against the force of spring 24.

This procedure continues until tip 10 has been mounted to nozzle 12 with sufficient force, at which time nozzle 12 also starts to move backwards against the force of spring 20. It is noted that for this embodiment of the invention, spring 20 engages a shoulder 22' on the nozzle 12 rather than a ring 22. Thus, as for the previous embodiment, the force with which tip 10 is mounted to nozzle 12 is controlled. When ejector sleeve 18' has been retracted to a position where shoulder 62 of flange 60 is adjacent shoulder 70 of slot 68, plate 66 may move under the force of the bias applied thereto by spring 67 to move shoulder 70 over shoulder 62, thereby engaging latch 30' to hold ejector sleeve 18' in the retracted position. As for the prior embodiment, this results in audio, tactile and visual feedback to the operator that the tip 10 is fully mounted and that the mounting operation may be terminated. Once the operator removes insertion pressure from the tip 10, spring 20 returns the nozzle 12 to the latched position shown in FIG. 2B.

When latch 30' is to be released, the operator presses on surface 82 of plate 66, moving the plate to its released position against the bias force applied thereto by spring 67. This moves shoulder 70 of slot 68 away from flange 60, permitting ejector sleeve 18' to be moved to its released position by spring 24. As for the prior embodiment, with spring 24 having a significantly greater force than spring 20, this results in shoulder 48 of the ejector sleeve 18' striking tip 10 with sufficient force to eject the tip 10 from nozzle 12.

Figure 2C:
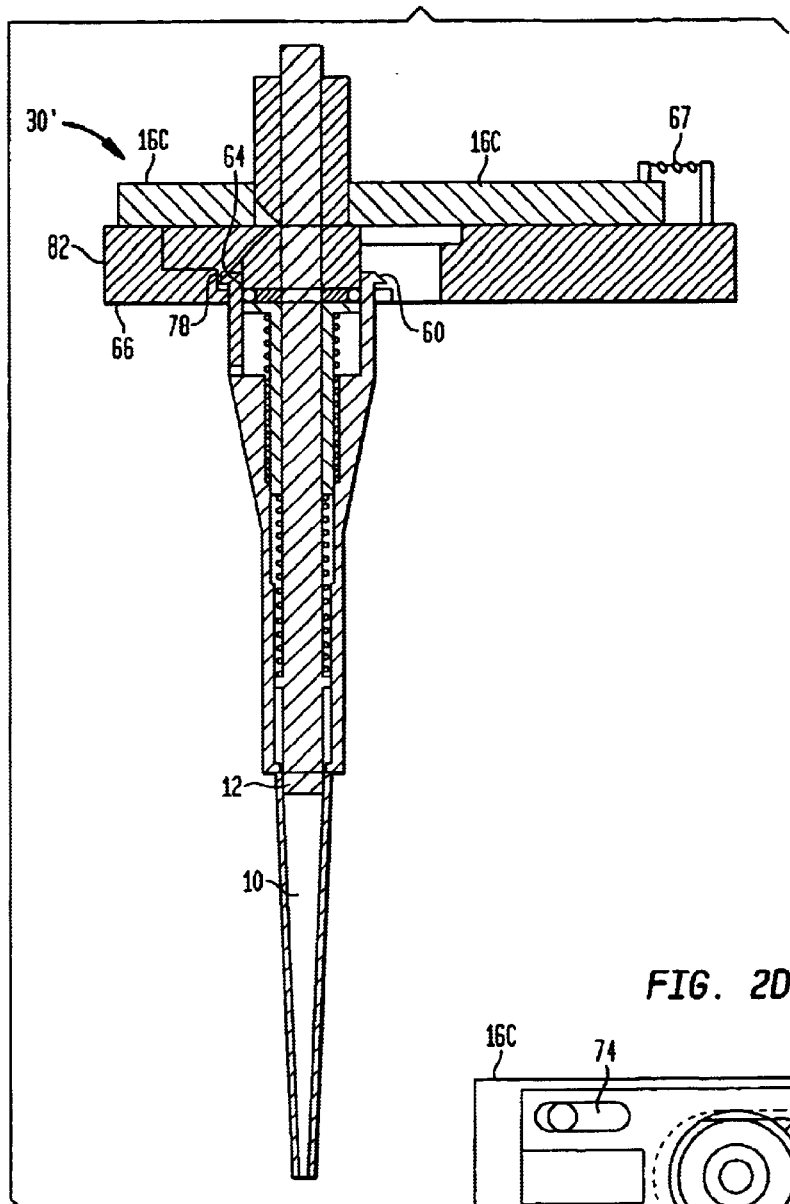
Figure 2D:
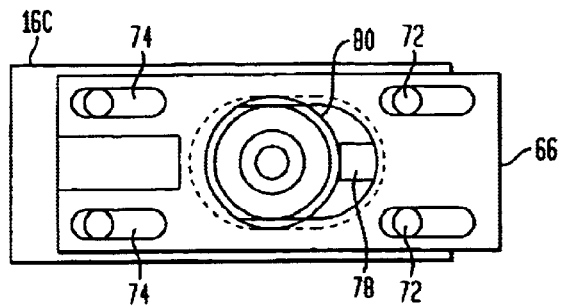
FIG. 2D is a sectional view taken along the line D—D in FIG. 2A.

However, in the event the tip 10 becomes stuck as shown in FIG. 2C, pressure may continue to be exerted on surface 82 to force angled or wedge surface 78 of insert 76 against angled surface 64 of flange 60. This applies a wedge overdrive force through sleeve 18' to tip 10 which supplements the force provided by spring 24 so as to facilitate the removal of a stuck tip 10, thereby permitting sleeve 18' to return to its fully released position.

FIGS. 3A–3D illustrate still another embodiment of the invention, which embodiment is utilized in conjunction with a pipette of the type described in application Ser. No.

Figure 3A:
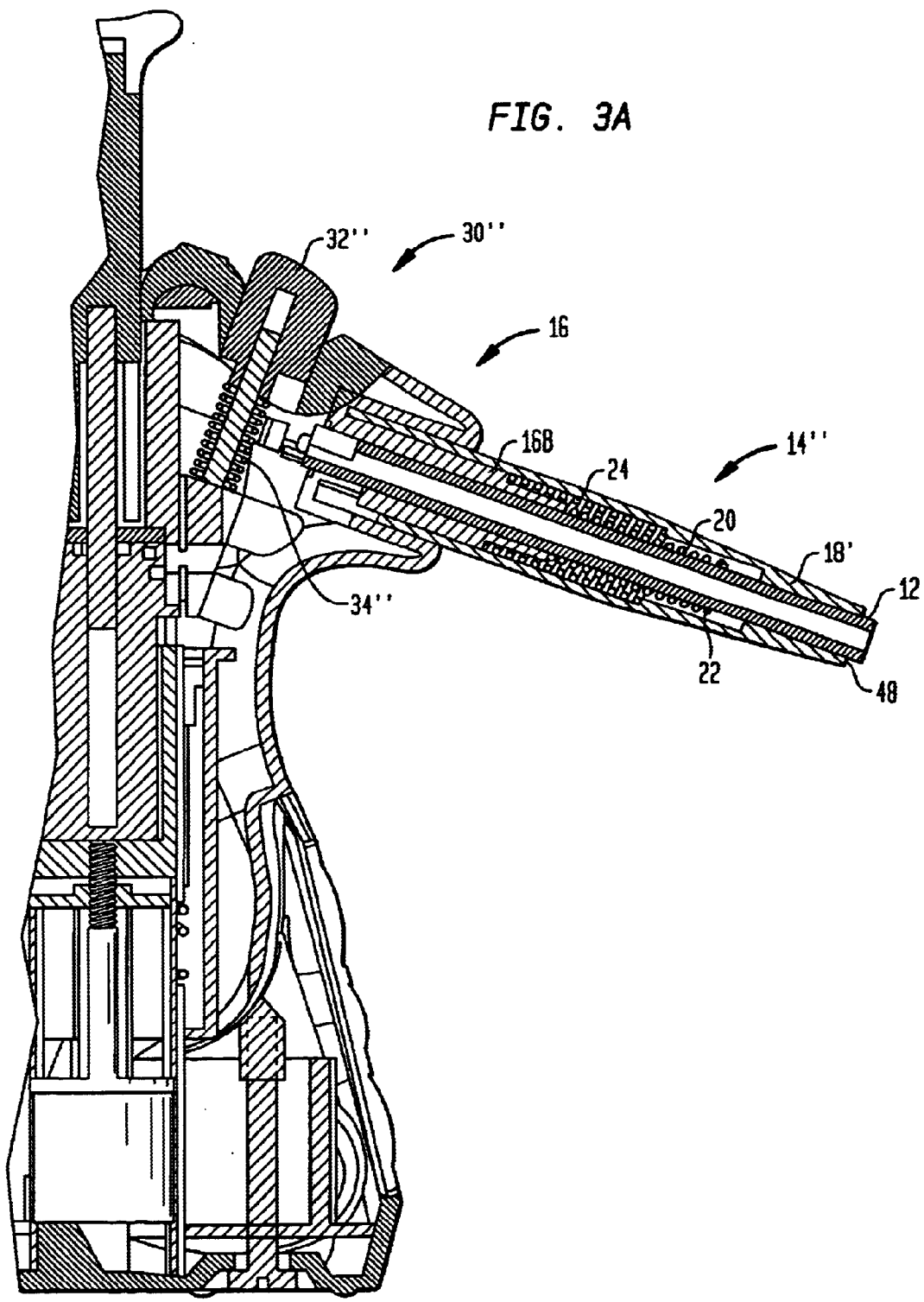
FIGS. 3A and 3B are a partial side sectional view and a top sectional view respectively for a third embodiment of the invention shown in the released position.
Figure 3B:
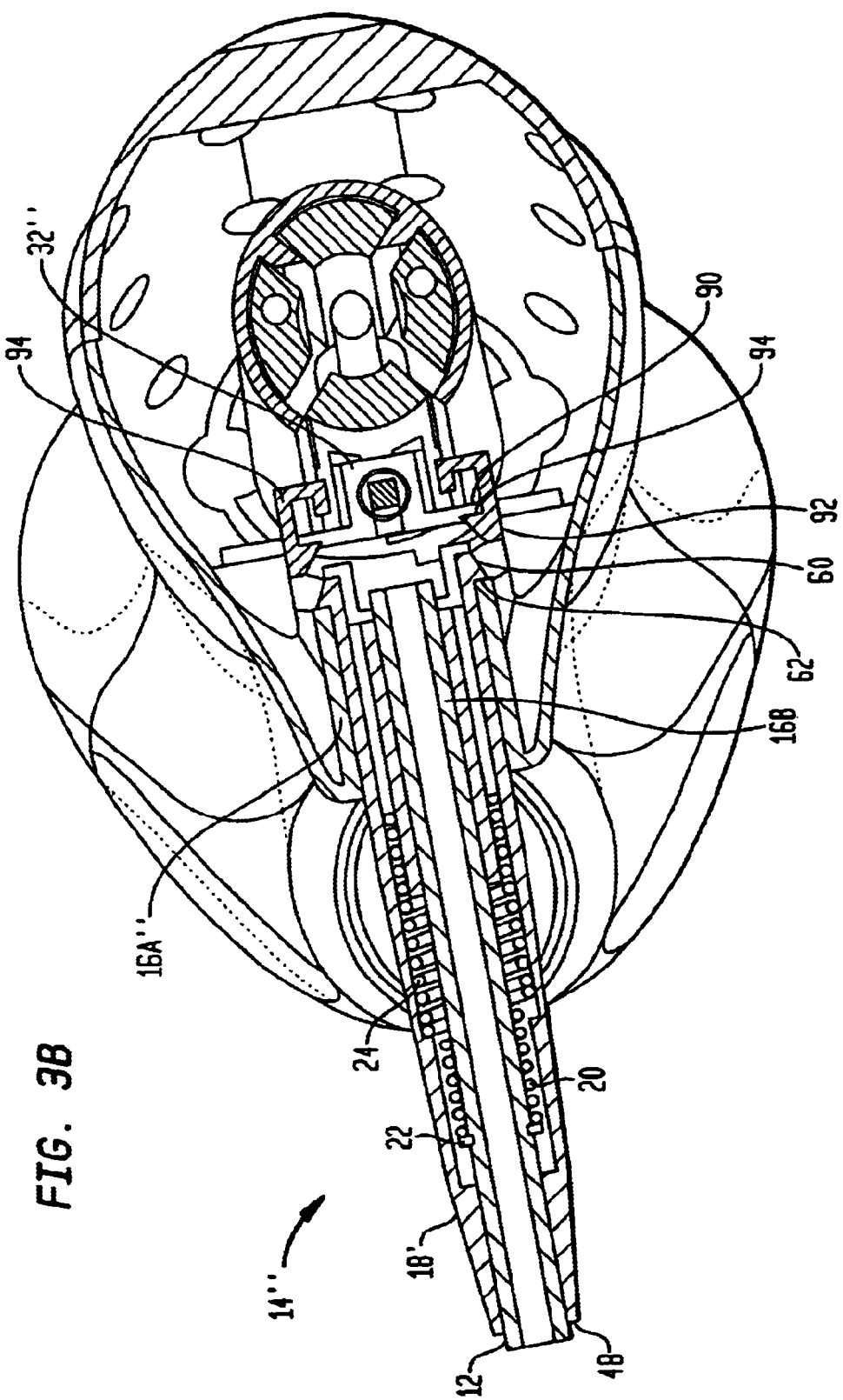
Figure 3C:
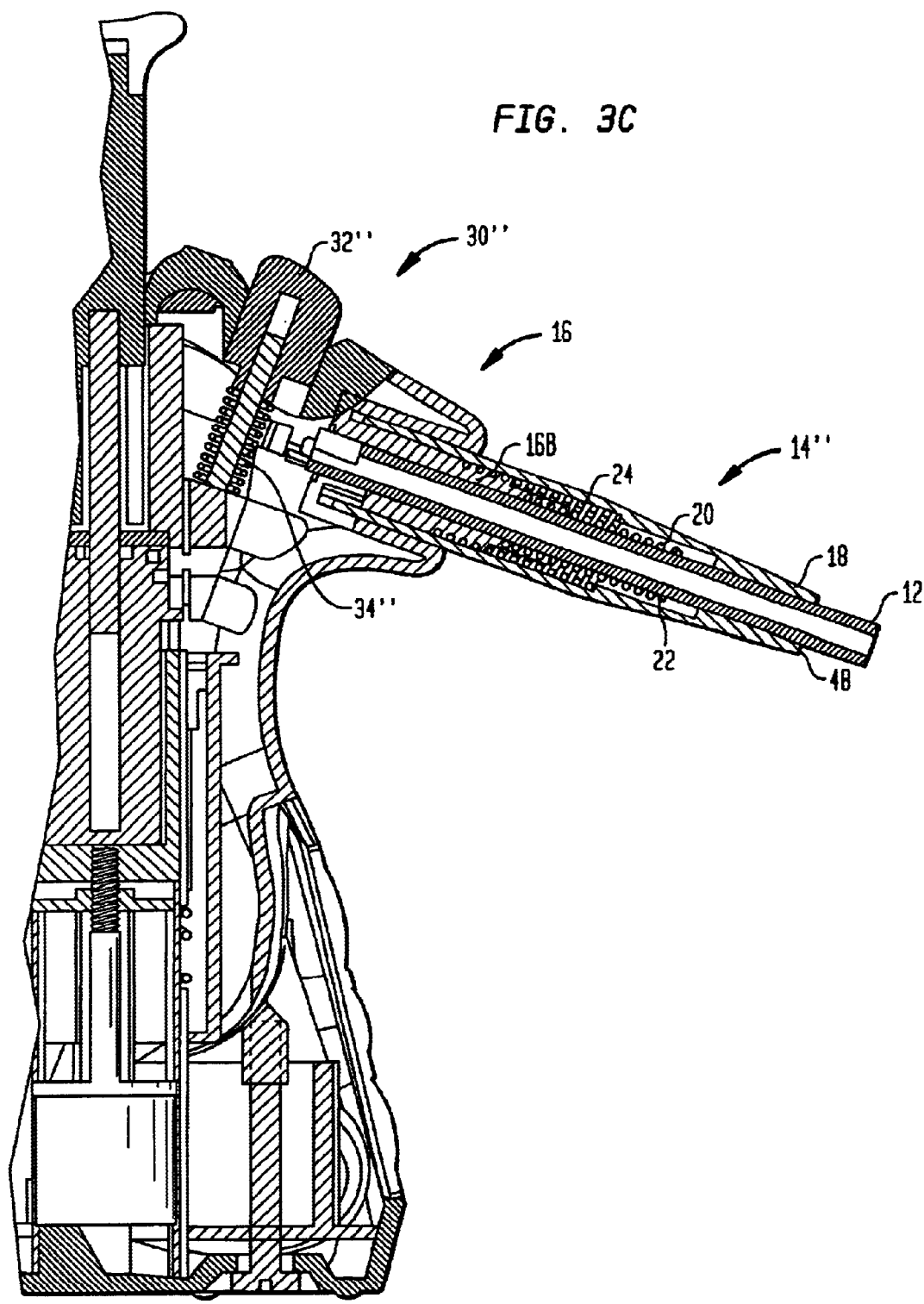
FIGS. 3C and 3D are the same views respectively of this embodiment in the latched position.
Figure 3D:
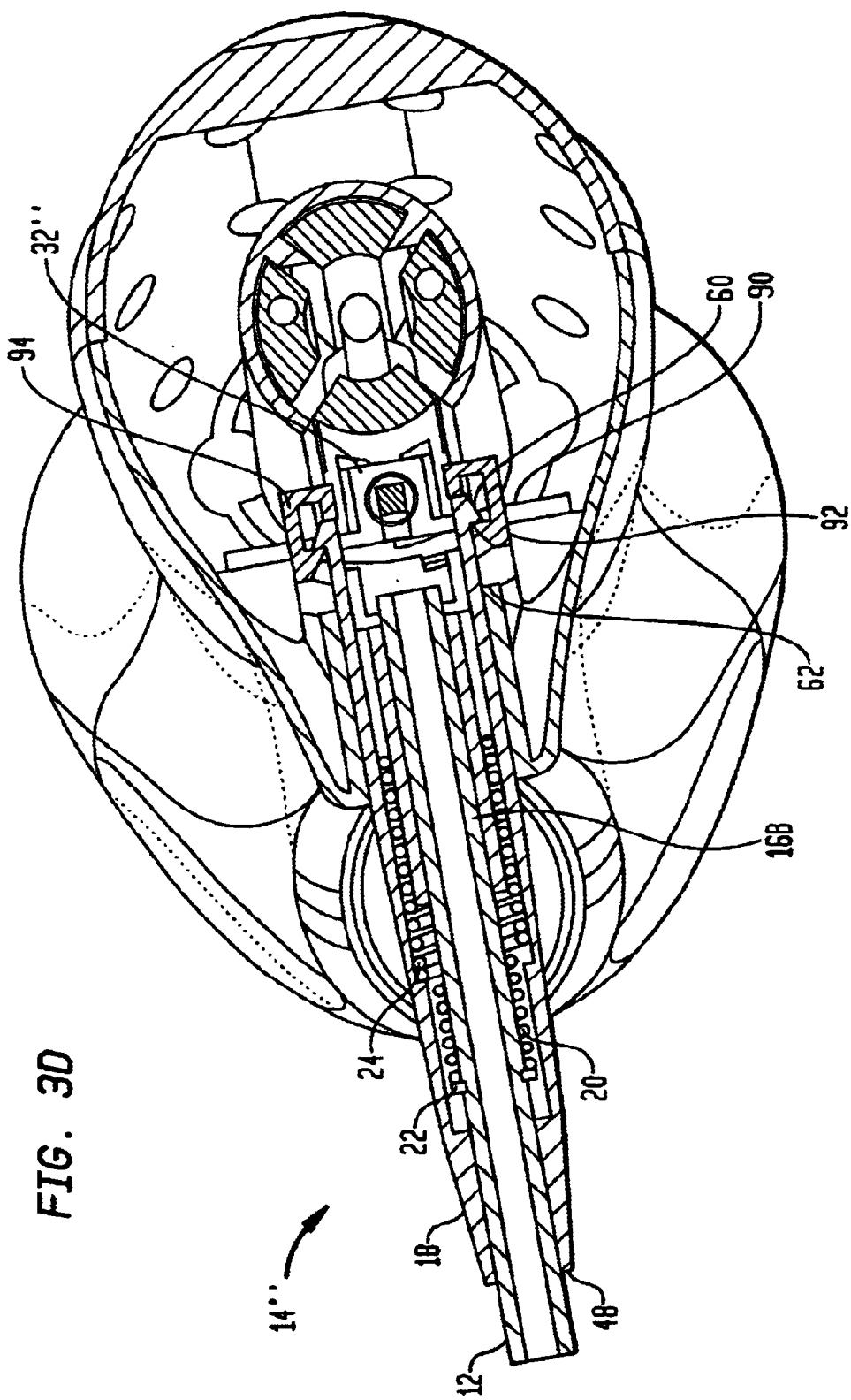

09/873,522 of the applicant entitled HAND HELD PIPETTE which is being filed concurrently herewith. As can be seen from these figures, the pipette of this embodiment is substantially the same as the pipettes of the prior embodiments except for the latching mechanism 30". For this embodiment of the invention, ejector sleeve 18' terminates in an angled flange 60 (FIG. 3B) having a shoulder 62 as for the embodiment of FIGS. 2A–2D. As shown in FIG. 3B, shoulder 62 engages an internal end of a housing component 16A" when the mechanism is in its released position to define the end position of the ejector sleeve 18'. When in a latched position, as seen in FIG. 3D, shoulder 62 engages shoulders 90 of flanges 92 at the end of fingers 94. When button 32" is depressed, fingers 94 are moved down to move flange 92, and shoulder 90 thereof, out of contact with shoulder 62 of flange 60, permitting ejector sleeve 18' to return to the release position in a manner previously described to effect the ejection of tip 10. FIG. 3C illustrates nozzle 12 in the latched position. Except as indicated above, the embodiment of FIGS. 3A–3D operates in substantially the same way as the embodiments previously described.

FIG. 4 illustrates an embodiment of the invention which may be used, either alone or in combination with the prior embodiments, to permit the type of tip 10 being mounted to the pipette to be automatically detected. For example, tips 10 may have different dimensions, for example different length, volume, shape, orifice size, etc., may have different surface treatment, including no treatment or for example a low liquid retention treatment, may have a filter or no filter, may have different filters, or may have other different features. Tip differences can require slight differences in pipette calibration, and use of the wrong tip can cause other problems. It is therefore desirable that the pipette be able to automatically detect the tip being mounted thereto both to facilitate proper calibration settings for the tip being used and to assure that the proper tip is being utilized. FIG. 4 illustrates how the movable sleeve 18 and other mechanisms described above can be adapted to also perform tip type detection.

Referring to FIG. 4, nozzle 12 is connected at a point remote from the tip 10, for example at the inner end of the nozzle 12, to a position detector 100, which is shown in the figure as a linear encoder 100. A sensor 102 is also provided to detect when sleeve 18 has moved by its full stroke. Where a latch 30 is provided, as for the previous embodiments, operation of the latch may be detected to indicate full stroke for the sleeve 18. In FIG. 4, sensor 102 includes a flag 104 mounted to move with sleeve 18 and a sensor 106, for example an optical sensor, which triggers when the flag 104 reaches the sensor 106. While not shown in FIG. 4 to simplify the figure, this embodiment would also include springs 20 and 24 and related components, and may include a latch 30 when also used as a detipper.

In operation, each different tip type is designed to have slightly different base diameter, taper or other base dimension which does not affect its function, but which changes the point on the tip 10 at which nozzle 12 makes contact with the tip 10 relative to the tip end making contact with shoulder 48 of sleeve 18. This may also be achieved by providing an internal ring or shoulder 108 or some other feature on the inside of the tip base, the spacing of such shoulder from the base end of the tip or some other characteristic of the feature being controlled to indicate the tip type. Other detectable variations in the tip base are also possible to provide an indication of tip type.

The variations in the tip base indicated above result in there being variations in the displacement of nozzle 12 for different tip types when sensor 102 indicates that a full stroke has occurred for sleeve 18. Thus, the reading from encoder 100 when sensor 102 generates an output can serve as an indication of tip type, a processor controlling the pipetting operation correlating the encoder reading with the appropriate tip type. Where only two tip types are used, encoder 100 may be a simple switch which is closed for the displacement D for one tip type, but not the other.

While the invention has been described above with respect to three illustrative detipper embodiments and one tip type detection embodiment, it is apparent that these embodiments are for purposes of illustration only and that various other modifications are possible in the implementation of the invention while still remaining within the spirit and scope thereof. For example, while three latching mechanisms 30, 30' and 30" have been shown, various other latching mechanisms for the ejector sleeve may also be employed. Similarly, while bias springs 20 and 24 have been used for biasing the nozzle and ejector sleeve respectively and springs 34, 34", 67 have been used to bias the latch mechanism, other biasing mechanism known in the art might also be employed.

Further, while the latch release buttons have been on the side of the pipette for illustrative embodiments, with appropriate modifications of the latch mechanism, the release button stroke could be parallel to the axis of the nozzle, or at some other appropriate angle thereto. Also, while the release buttons have been shown as being manually operable, automatic or semi-automatic release of the sleeve is also possible, for example in response to a pipetting operation being detected as completed, or for semi-automatic, in response to the operator closing a suitable contact. Where the tips are mounted in a rack from which they are mounted to the nozzle, an extending sleeve or other suitable element of the rack may co-act with shoulder 48 to retract ejector sleeve 18 to its latched position either instead of or in cooperation with tip 10. This mechanism may for example be employed in applications where the pipette has multiple nozzles to each of which tips are simultaneously mounted from a rack containing the tips. Other modifications in the detipping mechanism would be apparent to one skilled in the art.

Further, while the nozzles and tips have been shown as having mating conical external and internal surfaces respectively, this is also not a limitation on the invention, nozzles and/or tips having other shapes capable of mating and sealing also being usable. Selected features could appear on the tips and/or nozzle to facilitate mating and sealing. It is also possible that when, for example, the end of the tip contacts the sleeve, it triggers the release of the nozzle to enter the tip with a controlled force, slightly displacing the tip end from the sleeve. For detipping, the nozzle could be retracted under spring or other suitable force to engage the end of the tip mounted to the end of the nozzle against the shoulder of the sleeve to effect detipping. Other mechanisms for achieving relative motion between the nozzle and sleeve are also possible.

Similarly, while the detipping mechanisms and tip detection mechanisms can be used together, each can also be used independently of the other. Similarly, the detector or encoder 100 and sensor 102 used for tip detection and the location of such detector/sensor may vary with application, the specific such elements and locations discussed above being for purposes of illustration only. Similarly, a sleeve mechanism other than full sleeve 18 could be utilized as the ejector for detipping and/or for interacting with the tip and moving relative to the nozzle for tip identification.

Thus, while the invention has been particularly shown and described above with respect to several embodiments, these embodiments are for purposes of illustration only and the forgoing and other changes in form and detail may be made therein by one skilled in the art while still remaining within the spirit and scope of the invention which is to be defined only by the following claims:

What is claimed is:

1. A pipette including: a spring loaded nozzle to which a pipette tip may be removably mounted and a mechanism for facilitating the removal of the tip; said mechanism comprising:

a spring loaded ejector sleeve through which said nozzle passes, said sleeve terminating near an end of the nozzle to which the tip is mounted when the sleeve is in a normal position, the sleeve being moved away from said end of the nozzle against a spring load of the ejector sleeve when the tip is mounted to said nozzle, and said sleeve including a first latch portion which mates with a second latch portion of said pipette when said sleeve is in a retracted position to which said sleeve is moved when the tip is property mounted to said nozzle to hold said sleeve in said retracted position against said spring load of said ejector sleeve, and a third latch portion operable to unmate said first and second latch portions, freeing said sleeve to return in response to said spring load of said ejector sleeve to the normal position, the sleeve engaging said tip before reaching said normal position to facilitate the removal of the tip.

2. The mechanism as claimed in claim 1 including an overforce mechanism operable to supplement said spring load of said ejector sleeve in moving said sleeve to said normal position against a stuck tip to further facilitate removal of said tip.

3. The mechanism as claimed in claim 1 wherein said first latch portion is a keyhole slot formed in said sleeve, wherein said second latch portion is a detent having a large portion which fits in an enlarged portion of said slot when said sleeve is in the retracted position and a small portion sized to fit in a narrow portion of said slot, said narrow portion being adjacent said detent except when the sleeve is in the retracted position, and wherein said third latch portion is a button operable for moving said small portion of the detent into said narrow portion of said slot, whereby said sleeve becomes unlatched.

4. The mechanism as claimed in claim 3 wherein said detent is spring biased to move the large portion of the detent into said enlarged portion of said slot.

5. The mechanism as claimed in claim 1 wherein said first latch portion is a projection at a proximal end of said sleeve, said second latch portion is a mating lip on a latch plate biased to have the lip engage the projection when the sleeve is in the retracted position, and said third latch portion is a portion of said latch plate which is manually operable to move the plate against the bias to move said lip away from said projection, permitting said sleeve to return to the normal position.

6. The mechanism as claimed in claim 5 including an angled surface on said plate positioned to engage an angled surface associated with said sleeve when said latch plate is moved beyond a point where said lip no longer engages said projection to supplement said spring load in moving said sleeve to the normal position against a stuck tip to further facilitate removal of said tip.

7. The mechanism as claimed in claim 1 including a mechanism for controlling the force with which the tip is mounted to said nozzle.

8. The mechanism as claimed in claim 7 wherein said mechanism for controlling is operable for moving said nozzle away from a tip mounting force and against a bias spring.

9. The mechanism as claimed in claim 8 wherein said bias spring has less load than the spring load applied to said ejector sleeve.

10. The mechanism as claimed in claim 1 wherein said ejector sleeve is operable for being moved away from said end of the nozzle by said tip.

11. The mechanism as claimed in claim 1 wherein said ejector sleeve is operable for removing said tip when mounted in a rack of a plurality of tips having a protrusion adjacent each tip by said ejector sleeve is being moved away from said end of the nozzle by the protrusion adjacent the tip being mounted.

12. The mechanism as claimed in claim 1 wherein said first and second latch portions are operable for mating and are operable for generating an operator perceptible feedback output when mating.

13. The mechanism as claimed in claim 12 wherein said operator perceptible feedback output is at least one of an audible output and a tactile output.

14. A mechanism for facilitating the removal of a pipette tip from a pipette nozzle operable for moving inward as said tip is mounted to said nozzle; said mechanism comprising:

an ejector normally biased to a first position near an end of said nozzle to which said tip is mounted, and movable ms said tip is mounted to said nozzle against the bias, the ejector reaching a retracted position when the tip is fully mounted; and a latch for maintaining the ejector in said retracted position, said latch including a selectively operable latch release, the bias returning said ejector to said first position when said latch release is operated to facilitate ejection of the tip mounted to the nozzle.

15. The mechanism as claimed in claim 14 including an overforce mechanism operable to supplement said bias in moving said ejector to said normal position against a stuck tip to further facilitate removal of said tip.

16. The mechanism as claimed in claim 14 including a mechanism for controlling the force with which the tip is mounted to said nozzle.

17. The mechanism as claimed in claim 14 wherein the nozzle is operable for receiving a plurality of different tip types, each of which contacts both the ejector and the nozzle as a respective tip is mounted to the nozzle and moves the respective tip against a bias force, each tip type having a different base configuration which results in a difference in relative displacement of the nozzle to the ejector, and further comprising a mechanism for detecting such difference in the relative displacement to thus identify a tip type.

18. A mechanism for facilitating the removal of a pipette tip from a spring loaded pipette nozzle to which a pipette tip may be removably mounted; said mechanism comprising: a mechanism which stores mechanical energy when the tip is mounted to said nozzle, and which is operable to release the stored mechanical energy when the tip is to be removed to facilitate removal of said pipette tip, said mechanism for storing includes a latching mechanism operative when said mechanical energy is fully stored, and operative for generating an operator detectable output.

19. The mechanism as claimed in claim 18 including a mechanism which limits the force with which the tip is mounted to the nozzle.

20. The mechanism as claimed in claim 18 including an overforce mechanism for further facilitating removal of a stuck tip.

21. In a pipette having a nozzle to which a tip may be removably mounted, a mechanism for facilitating the removal of the tip from the nozzle including:

a spring loaded ejector sleeve through which said nozzle passes, said sleeve terminating near an end of the nozzle to which a tip is mounted when the sleeve is in a normal position, the sleeve being moved away from said end of the nozzle against a spring load when the tip is mounted to said nozzle; and said sleeve including a first latch portion which mates with a second latch portion of said pipette when said sleeve is in a retracted position to which said sleeve is moved when the tip is properly mounted to said nozzle to hold said sleeve in said retracted position against said spring load, and a third latch portion operable to unmate said first and second latch portions, freeing said sleeve to return in response to said spring load to the normal position, the sleeve engaging said tip before reaching said normal position to facilitate the removal of the tip, wherein said first latch portion is a keyhole slot formed in said sleeve, said second latch portion is a detent having a large portion which fits in an enlarged portion of said slot when said sleeve is in the retracted position and a small portion sized to fit in a narrow portion of said slot, said narrow portion being adjacent said detent except when the sleeve is in the retracted position, and said third latch portion is a button operable for moving said small portion of the detent into said narrow portion of said slot, whereby said sleeve becomes unlatched.

22. In a pipette having a nozzle to which a tip may be removably mounted, a mechanism for facilitating the removal of the tip from the nozzle including:

a spring loaded ejector sleeve through which said nozzle passes, said sleeve terminating near an end of the nozzle to which a tip is mounted when the sleeve is in a normal position, the sleeve being moved away from said end of the nozzle against a spring load when the tip is mounted to said nozzle; and said sleeve including a first latch portion which mates with a second latch portion of said pipette when said sleeve is in a retracted position to which said sleeve is moved when the tip is properly mounted to said nozzle to hold said sleeve in said refracted position against said spring load, and a third latch portion operable to unmate said first and second latch portions, freeing said sleeve to return in response to said spring load to the normal position, the sleeve engaging said tip before reaching said normal position to facilitate the removal of the tip, wherein said first latch portion is a keyhole slot formed in said sleeve, wherein said second latch portion is a detent having a large portion which fits in an enlarged portion of said slot when said sleeve is in the retracted position and a small portion sized to fit in a narrow portion of said slot, said narrow portion being adjacent said detent except when the sleeve is in the retracted position, said third latch portion is a button operable for moving said small portion of the detent into said narrow portion of said slot, whereby said sleeve becomes unlatched, and said detent is spring biased to move the large portion of the detent into said enlarged portion of said slot.

23. In a pipette having a nozzle to which a tip may be removably mounted, a mechanism for facilitating the removal of the tip from the nozzle including:

a spring loaded ejector sleeve through which said nozzle passes, said sleeve terminating near an end of the nozzle to which a tip is mounted when the sleeve is in a normal position, the sleeve being moved away from said end of the nozzle against a spring load when the tip is mounted to said nozzle; and said sleeve including a first latch portion which mates with a second latch portion of said pipette when said sleeve is in a retracted position to which said sleeve is moved when the tip is properly mounted to said nozzle to hold said sleeve in said retracted position against said spring load, and a third latch portion operable to unmate said first and second latch portions, freeing said sleeve to return in response to said spring load to the normal position, the sleeve engaging said tip before reaching said normal position to facilitate the removal of the tip, wherein said first latch portion is a keyhole slot formed in said sleeve, wherein said first latch portion is a projection at a proximal end of said sleeve, said second latch portion is a mating lip on a latch plate biased to have the lip engage the projection when the sleeve is in the retracted position, and said third latch portion is a portion of said latch plate which is manually operable to move the plate against the bias to move said lip away from said projection, permitting said sleeve to return to the normal position.

24. In a pipette having a nozzle to which a tip may be removably mounted, a mechanism for facilitating the removal of the tip from the nozzle including:

a spring loaded ejector sleeve through which said nozzle passes, said sleeve terminating near an end of the nozzle to which a tip is mounted when the sleeve is in a normal position, the sleeve being moved away from said end of the nozzle against a spring load when the tip is mounted to said nozzle; and said sleeve including a first latch portion which mates with a second latch portion of said pipette when said sleeve is in a retracted position to which said sleeve is moved when the tip is properly mounted to said nozzle to hold said sleeve in said retracted position against said spring load, and a third latch portion operable to unmate said first and second latch portions, freeing said sleeve to return in response to said spring load to the normal position, the sleeve engaging said tip before reaching said normal position to facilitate the removal of the tip, wherein said first latch portion is a keyhole slot formed in said sleeve, wherein said first latch portion is a projection at a proximal end of said sleeve, said second latch portion is a mating lip on a latch plate biased to have the lip engage the projection when the sleeve is in the retracted position, and said third latch portion is a portion of said latch plate which is manually operable to move the plate against the bias to move said lip away from said projection, permitting said sleeve to return to the normal position, and including an angled surface on said plate positioned to engage an angled surface associated with said sleeve when said latch plate is moved beyond a point where said lip no longer engages said projection to supplement said spring load in moving said sleeve to the normal position against a stuck tip to further facilitate removal of said tip.

25. A mechanism for facilitating the removal of a pipette tip from a spring loaded pipette nozzle, the nozzle being moved against a spring load when the pipette tip is mounted to the nozzle; said mechanism, comprising:

a spring loaded ejector sleeve through which the nozzle passes, the ejector sleeve terminating near an end of the nozzle to which the pipette tip is mounted when the ejector sleeve is in a normal position, the ejector sleeve being moved against a spring load of said ejector sleeve when the pipette tip is mounted to the nozzle; and said sleeve including a first latch portion which mates with a second latch portion when the ejector sleeve is in a retracted position to which the ejector sleeve is moved when the pipette tip is properly mounted to the nozzle to hold the ejector sleeve in the retracted position against the spring load of said ejector sleeve, and a third latch portion operable to unmate the first and second latch portions, freeing the ejector sleeve to return in response to the spring load of said ejector sleeve to the normal position, the ejector sleeve engaging the pipette tip before reaching the normal position to facilitate the removal of the pipette tip.

26. A pipette including a spring loaded nozzle to which a pipette tip may be removably mounted and a mechanism for facilitating the removal of the tip; said mechanism comprising:

a spring loaded ejector sleeve through which the nozzle passes;

wherein said spring loaded ejector sleeve is operable to be retracted and advanced to facilitate the removal of a tip mounted to said nozzle.

27. The mechanism as claimed in claim 26, wherein the ejector sleeve includes a first latch portion and further comprising:

a second latch portion which mates with the first latch portion when the ejector sleeve is in a refracted position to which the ejector sleeve is moved when the pipette tip is properly mounted to the nozzle to hold the ejector sleeve in the retracted position against a spring load of said ejector sleeve; and a third latch portion operable to unmate the first latch portion and the second latch portion, freeing the ejector sleeve to return in response to the spring load of said ejector sleeve to a normal position, the ejector sleeve engaging the pipette tip before reaching the normal position to facilitate the removal of the pipette tip.

* * * * *